United States Patent
McIntyre

(10) Patent No.: US 8,568,385 B2
(45) Date of Patent: Oct. 29, 2013

(54) DEVICE AND METHOD FOR RESTRICTING BLOOD FLOW TO FIBROIDS

(75) Inventor: Jon T. McIntyre, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 677 days.

(21) Appl. No.: 12/207,197

(22) Filed: Sep. 9, 2008

(65) Prior Publication Data

US 2009/0227982 A1 Sep. 10, 2009

Related U.S. Application Data

(60) Provisional application No. 60/971,434, filed on Sep. 11, 2007.

(51) Int. Cl.
*A61M 31/00* (2006.01)
*A61M 29/00* (2006.01)

(52) U.S. Cl.
USPC ........ 604/515; 604/514; 604/96.01; 604/509; 604/97.01; 606/192; 606/193

(58) Field of Classification Search
USPC .......... 604/96.01, 515, 96.02–103.14, 41, 48, 604/500, 508, 509, 511, 187; 606/193, 192; 128/898
See application file for complete search history.

(56) References Cited

U.S. PATENT DOCUMENTS

| | | | |
|---|---|---|---|
| 4,207,891 A | 6/1980 | Bolduc | |
| 5,304,123 A * | 4/1994 | Atala et al. | 604/514 |
| 5,328,471 A | 7/1994 | Slepian | |
| 5,458,574 A * | 10/1995 | Machold et al. | 604/101.03 |
| 5,728,132 A | 3/1998 | Van Tasswel et al. | |
| 5,904,665 A | 5/1999 | Muharib | |
| 6,409,716 B1 | 6/2002 | Sahatjian et al. | |
| 6,550,482 B1 * | 4/2003 | Burbank et al. | 128/898 |
| 6,676,680 B1 | 1/2004 | Packer | |
| 6,689,148 B2 * | 2/2004 | Sawhney et al. | 606/193 |
| 2003/0195464 A1 | 10/2003 | Sahatjian et al. | |
| 2005/0015047 A1 | 1/2005 | Shah | |
| 2005/0113857 A1 * | 5/2005 | Nohilly et al. | 606/193 |
| 2006/0173486 A1 * | 8/2006 | Burke et al. | 606/193 |
| 2006/0213526 A1 * | 9/2006 | McIntyre | 128/898 |
| 2008/0249534 A1 * | 10/2008 | Gruber et al. | 606/119 |

FOREIGN PATENT DOCUMENTS

WO 97/27810 8/1997

* cited by examiner

*Primary Examiner* — Emily Schmidt
*Assistant Examiner* — Bradley G Thomas, Jr.
(74) *Attorney, Agent, or Firm* — Fay Kaplun & Marcin, LLP

(57) ABSTRACT

A method of treating tissue comprises introducing into a hollow organ a support device and, after insertion, arranging the support device into a non-yielding configuration substantially filling the hollow organ and substantially preventing walls of the hollow organ from moving inward in combination with inducing contraction of the hollow organ around the support device to cut off blood flow through at least a portion of the walls of the hollow organ and removing the support device after blood flow has been cut off for a predetermined time. A system to treat tissue comprises a support device which, in a first configuration, is sized and shaped for insertion into a hollow organ and an expansion mechanism for expanding the support device from the first configuration to a second configuration in which the support device substantially fills the hollow organ providing a non-yielding support so that, if the hollow organ is contracted around the support device, blood flow through at least a portion of a wall of the hollow organ is cut off.

15 Claims, 2 Drawing Sheets

DEVICE AND METHOD FOR RESTRICTING BLOOD FLOW TO FIBROIDS

PRIORITY CLAIM

This application claims priority to U.S. Provisional Application Ser. No. 60/971,434 entitled "Device and Method for Restricting Blood Flow to Fibroids," filed on Sep. 11, 2007. The Specification of the above-identified application is incorporated herewith by reference.

BACKGROUND

Uterine fibroids are a common condition resulting in abnormal menstrual bleeding and pain. Conventional treatments to alleviate symptoms associated with fibroids include drug therapies which are more suited for less advanced cases and hysterectomy which are typically performed only for more advanced cases. Less invasive procedures are available which typically entail fewer side effects, shorter hospital stays and reduced discomfort.

For example, fibroids may be ablated using electrical energy, heat or cryogenic cooling probes, as well as by occluding the blood supply thereto. Ablation procedures typically require the physician to locate each fibroid and treat it separately which complicates the procedures and introduces the risk that one or more fibroids may go untreated. Vascular occlusion procedures include uterine fibroid embolization (UFE) where embolic spheres are injected into the uterine arteries to prevent blood supply to the fibroids, surgical treatments requiring incisions to reach the affected area to procedures involving the permanent placement of a device or devices accurately over a target anatomical structure (e.g., clamping a blood vessel supplying the fibroid(s)), and less invasive temporary clamping of the uterine arteries that may not require any incisions. Those skilled in the art will understand that patient discomfort and a risk of infection are associated with all procedures requiring incisions. In addition, when a device (e.g., a clamp) has been placed over target tissue for temporary non-incisional treatment, the patient must be kept still for the 6 hours or more during which blood flow is to be occluded. In addition, the clamping may damage the blood vessel(s).

SUMMARY OF THE INVENTION

In one aspect, the present invention is directed to a method of treating tissue comprising introducing into a hollow organ a support device and, after insertion, arranging the support device into a non-yielding configuration substantially filling the hollow organ and substantially preventing walls of the hollow organ from moving inward. After this, contraction of the hollow organ around the support device is induced to cut off blood flow through at least a portion of the walls of the hollow organ and the support device is removed after blood flow has been cut off for a predetermined time.

DETAILED DESCRIPTION

Figure 1:
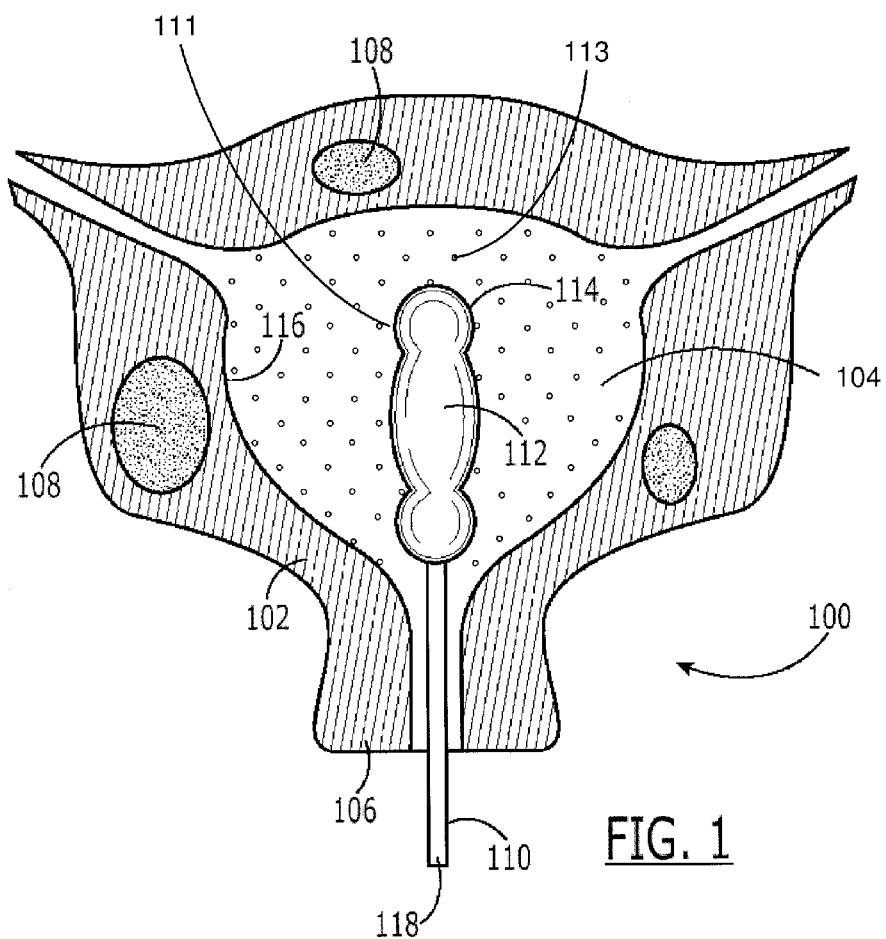
FIG. 1 is a sectional view showing a deflated balloon within an uterus according to the invention.

The present invention may be further understood with reference to the following description and to the appended drawings, wherein like elements are referred to with the same reference numerals. The present invention relates to devices for reducing or stopping blood flow to fibroids within an organ (i.e. the uterus) or to any target tissue. That is, the present invention may be useful in treating tissue in any hollow organ which may be induced to contract around a support structure introduced thereinto. For example, the present invention may be useful in treatment of the bladder and/or prostate. In particular the present invention relates to devices compressing the uterus to stop blood flow to uterine fibroids.

Exemplary embodiments of the invention provide a method and system for treating fibroids through less complex surgical procedures which reduce recovery time and patient discomfort. According to the invention, fibroids are treated by filling the uterine cavity with a device that provides a non yielding surface upon which the uterus can rest. The uterus is then caused to contract over the non yielding surface, so that the uterine tissue is compressed and the blood supply through the uterine tissue (i.e., the supply to the fibroids) is interrupted. The contraction is maintained for a period of time selected so that all fibroids present in the uterus necrose and so that no permanent damage is caused to non-targeted tissue.

Figure 2:
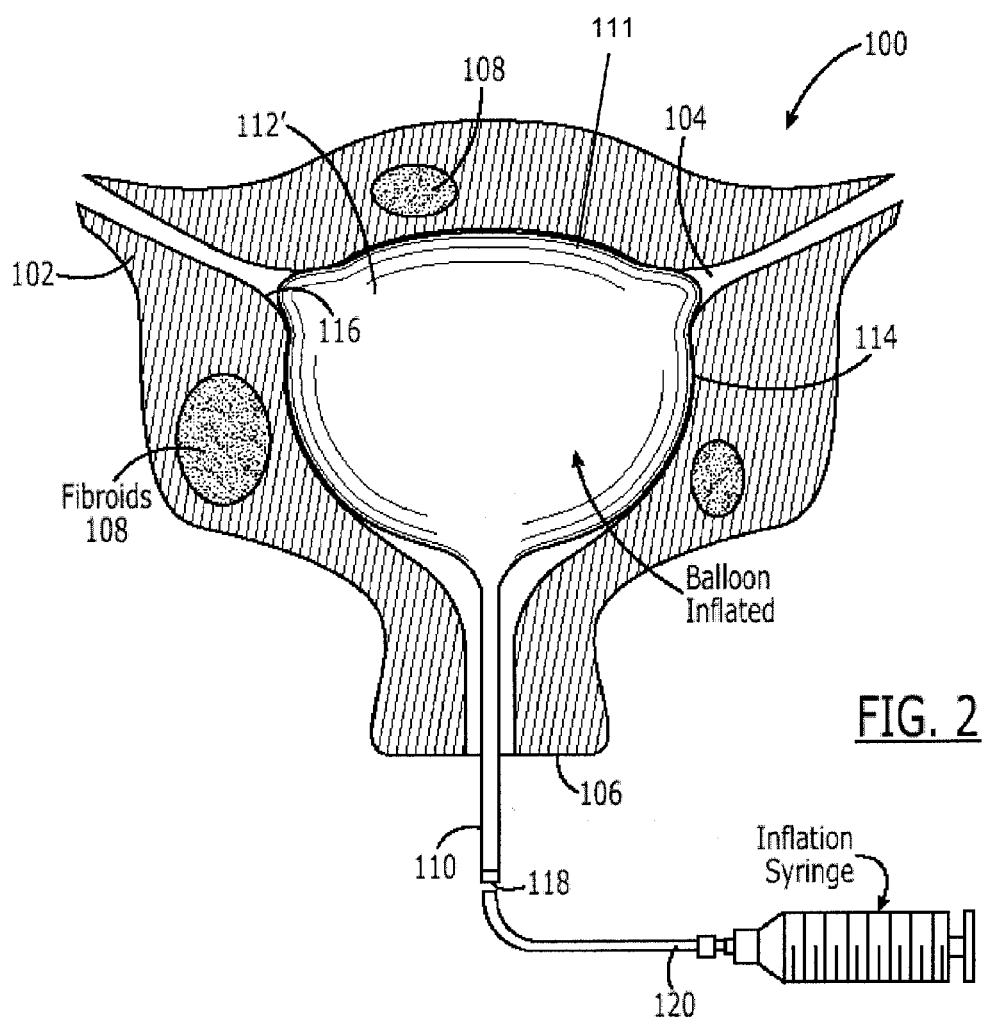
FIG. 2 is a sectional view showing the balloon of FIG. 1 inflated according to the invention.

FIGS. 1 and 2 show a system 100 for restricting blood flow according to an exemplary embodiment of the invention. The system 100 comprises devices used to treat fibroids 108 that have formed in the walls of a uterus 102. The system 100 includes a support device 111 which in this embodiment is an inflatable element 112 (e.g., a balloon) which is inserted into the uterine cavity 104 in a deflated state as shown in FIG. 1 and which is then inflated as shown in FIG. 2 to form a non-yielding support abutting the walls of the uterus 102. The exemplary inflatable element 112 is coupled to an inflation shaft 110 that extends proximally away from the inflatable element 112 so that, when the inflatable element 112 is in a desired position within the uterus, a proximal end of the inflation shaft 110 extends out of the body (e.g., via the cervix through the vagina) with an inflation port formed, for example, in a connector 118 thereof is accessible to a user of the system 100. As would be understood by those skilled in the art, the connector 118 facilitates connection of the inflation shaft 110 and, consequently, the inflatable element 112 with a source of inflation fluid (e.g., syringe 120).

Prior to and during insertion into the uterine cavity 104, the inflatable element 112 is in the deflated state shown in FIG. 1, and is wrapped around the inflation shaft 110. The inflation shaft 110 and the deflated inflatable element 112 are inserted into the uterine cavity, for example, via the working channel of a hysteroscope. Then, after the inflatable element 112 has reached a desired position, inflation fluid is supplied to the proximal end of the inflation shaft 110 (e.g., via a hand operated syringe 120 or any other known inflation device) to inflate the inflatable element 112 to form a non-yielding support that substantially espouses a shape of inner walls 116 of the uterus 102. As would be understood by those skilled in the art, the inflation fluid may be, for example, saline or any other biocompatible, incompressible fluid.

Furthermore, as would be understood by those skilled in the art, the inflatable element 112 may be formed of any suitable elastic, biocompatible material. For example, the balloon material may be PET, PVC, PE, silicon, latex, polyurethane, nylon or another polymer or combination of polymeric materials. The material of which the inflatable element 112 is formed is also preferably selected to facilitate insertion together with the inflation shaft 110 into the uterine cavity 104 through a working channel of an hysteroscope. PE may facilitate insertion of the inflatable element 112. Alternatively, lubricious coatings may be applied to any of the above-listed materials to facilitate insertion. As would be understood by those skilled in the art, suitable hydrophilics are well established in the industry.

In a different embodiment, the support device 111 comprises a gel material 113 which is inserted into the uterus 102 as a yielding fluid that easily flows into the uterine cavity 104 to substantially fill it. After insertion, the gel material 113 is solidified using conventional procedures to form a non-yielding surface of the support device 111 for the uterus inner surface 116. Then, after the procedure has been completed, the gel material 113 is liquified or dissolved in a liquid by introducing an appropriate liquefying agent or solvent into the uterus 102, or by other conventional methods for removal from the uterine cavity 104. The gel material 113 may, for example be either of a lower critical solution temperature (LCST) material or a cross-linkable polymer as described in U.S. Pat. No. 6,663,594, the entire disclosure of which is hereby expressly incorporated by reference.

According to the invention, after the support device 111 has been inserted into the uterus to provide a non-yielding support, the uterus 102 is caused to contract therearound. As described above, the support device 111 may be an inflatable balloon, a solidified gel or any other element which may be inserted into the uterus to support the uterine walls in a current position and to resist any compression of the uterus. Cramping or contraction of the uterus 102 are then induced through the administration of any suitable medical agent adapted to cause muscular contraction as would be understood by those skilled in the art. The agent may include, for example, Pitocin which is often administered to cause uterine contraction (e.g., during childbirth to induce labor or postpartum to accelerate delivery of the placenta and to minimize post-partum hemorrhaging). As would be understood by those skilled in the art, Pitocin is a synthetic form of Oxytocin which is produced naturally by the body.

As the wall of the uterus 102 is compressed against the outer surface 114 of the inflated inflatable element 112 or other support device 111, the flow of blood through vessels in the wall of the uterus 102 is pinched off interrupting the supply of blood to the fibroids 108. Experimental data acquired using a transvaginal clamp to occlude the uterine arteries shows occlusion for a period of about 6 hours or greater is sufficient to necrose the fibroids 108 without a permanent negative effect on non-targeted "normal" tissue of the myometrium. Thus negative side effects are minimized. Contraction of the uterus 102 is preferably maintained over the support device 111 for a period of time selected to achieve a desired degree of treatment of the target tissue (e.g., fibroids 108). As stated above, to necrose the fibroids 108, contraction about the support device 111 is preferably maintained for 6 hours or more.

To alleviate discomfort, the patient may be heavily sedated or placed under general anesthesia during the procedure. Alternatively, to reduce recovery time, the procedure may be performed using an epidural anesthetic. Those skilled in the art will understand that the expected length of a procedure may be a factor in determining the type of sedation used.

After the uterus 102 has contracted over the non-yielding support device 111 for the desired amount of time, the contraction may be reversed by, for example, administering a medical compound countering the effect of the compression inducing agent (e.g., Pitocin). Alternatively, the administration of pitocin may be calibrated to lose efficacy after a desired period of time has elapsed. The support device 111 may then be withdrawn from the uterus 102 as described above. The uterus may also contract on its own as a result of the stretching caused by inflating a balloon within the cavity. For example, the balloon may be oversized to overstretch the uterus slightly to induce contraction.

The system 100 according to the present invention may be used employed to treat target tissue 108 (e.g., fibroids) according to the following exemplary steps. Initially, as would be understood by those skilled in the art, the patient may be sedated using general anesthesia or an epidural anesthetic. This initial step may be optional, depending on the expected duration of the procedure. A support element 111 is then introduced into the uterus 102, for example through the working channel of an hysteroscope, in an insertion configuration. In the insertion configuration the support element may yield if a pressure is applied thereto. The support element 111 is then acted upon to form a non yielding surface, for example by hardening a gel inserted in the uterus 102 or by inflating a balloon 112 of the device with a non compressible fluid.

Once the non yielding surface is in place, the walls 116 of the uterus 102 are caused to contract over the non yielding element. This may be achieved, for example, by administering picotin or another similar compound. The contracting uterus is compressed against the non yielding element, preventing the flow of blood. The contraction is maintained for a desired period of time, sufficient to necrose the uterine fibroids, but not the non targeted tissue of the uterus. After the desired time interval, the contraction is released, and the non yielding element is removed from the uterus. For example, the fluid is released from the inflatable balloon 112, or the gel is liquefied again.

The present invention has been described with reference to specific exemplary embodiments. Those skilled in the art will understand that changes may be made in details, particularly in matters of shape, size, material and arrangement of parts. Accordingly, various modifications and changes may be made to the embodiments. The specifications and drawings are, therefore, to be regarded in an illustrative rather than a restrictive sense.

What is claimed is:

1. A method for treating tissue, comprising:
   introducing a support device into a hollow organ;
   arranging the support device into a non-yielding configuration substantially filling the hollow organ and substantially preventing walls of the hollow organ from moving inward;
   inducing contraction of the hollow organ around the support device to cut off blood flow through at least a portion of the walls of the hollow organ; and
   removing the support device after blood flow has been cut off for a predetermined time.

2. The method of claim 1, wherein introducing the support device into the hollow organ includes inserting an inflatable element into the hollow organ in a deflated configuration.

3. The method of claim 2, wherein the inflatable element is inflated via an inflation shaft, which extends proximally from the balloon with a proximal end of the inflation shaft extending out of the hollow organ via a natural body passage opening into the organ.

4. The method of claim 1, wherein introducing the support device into the hollow organ includes inserting a gel material, in a fluid form, into the hollow organ such that the gel material substantially fills the hollow organ.

5. The method of claim 1, wherein arranging the support device includes solidifying the gel material into the non-yielding configuration.

6. The method of claim 1, wherein removing the support device includes administering one of a liquefying agent and a solvent into the hollow organ to liquefy the gel material.

7. The method of claim 1, wherein inducing contraction of the hollow organ includes administering a medical agent adapted to cause muscular contraction.

8. The method of claim 1, further comprising reversing the contraction of the hollow organ by administering a medical agent countering the contraction.

9. The method of claim 1, the hollow organ being the uterus and the tissue to be treated including at least one fibroid.

10. The method of claim 1 further comprising maintaining the contraction of the uterus from 6 to 24 hours.

11. A system for treating a tissue, comprising:
a support device including a gel material which, in a liquefied configuration, is inserted into a hollow organ; and
an insertion mechanism inserting a solidifying agent into the support device to transition the gel material from the liquefied configuration to a solidified configuration in which the support device substantially fills and overstretches the hollow organ providing a sufficiently non-yielding support so that, muscular contraction of the hollow organ around the support device restricts blood flow through at least a portion of the hollow organ.

12. The system of claim 11, wherein the gel material returns to the liquefied configuration upon inserting a liquefying agent into the support device.

13. A support device for treating tissue, comprising:
a support element including a gel material inserted into a hollow organ in a liquefied configuration; and
an insertion shaft extending proximally from the support element such that when the support element is inserted into the hollow organ a proximal end of the insertion shaft extends out of the hollow organ, the gel material being solidified into a solidified configuration by administering a solidifying agent via the insertion shaft wherein, when in the solidified configuration, the support element overstretches walls of the hollow organ and is sufficiently non-yielding that muscular contraction of the hollow organ around the support element restricts blood flow through at least a portion of the hollow organ.

14. The device of claim 13, wherein the gel material returns to the liquefied configuration upon inserting a liquefying agent into the gel material.

15. A support device for treating tissue, comprising a gel material insertable into a hollow organ in a yielding configuration such that the gel material substantially fills the hollow organ, the gel material being adapted to solidify into a non-yielding configuration in which the support device overstretches and supports walls of the hollow organ and resist compression of the hollow organ wherein, when in the non-yielding configuration, the gel material is sufficiently non-yielding that muscular contraction of the hollow organ around the gel material restricts blood flow through at least a portion of a wall of the hollow organ.

* * * * *